United States Patent [19]

Orejola

[11] Patent Number: 4,985,014
[45] Date of Patent: Jan. 15, 1991

[54] VENTRICULAR VENTING LOOP

[76] Inventor: Wilmo C. Orejola, 1012 Black Oak Ridge Rd., Wayne, N.J. 07470

[21] Appl. No.: 378,267

[22] Filed: Jul. 11, 1989

[51] Int. Cl.$^5$ ............................................. D01N 1/362
[52] U.S. Cl. ........................................ 600/16; 604/43
[58] Field of Search .................. 606/16; 604/4, 8, 9, 604/27, 43, 95, 96, 131, 151

[56] References Cited

U.S. PATENT DOCUMENTS

| | | | |
|---|---|---|---|
| 3,995,617 | 12/1976 | Watkins et al. | 600/16 |
| 4,116,589 | 9/1978 | Rishton | 600/18 |
| 4,129,129 | 12/1978 | Amrine | 604/43 |
| 4,548,597 | 10/1985 | Nelson | 604/43 |

FOREIGN PATENT DOCUMENTS

| | | | |
|---|---|---|---|
| 2233293 | 7/1973 | Fed. Rep. of Germany | 600/76 |
| 286145 | 11/1970 | U.S.S.R. | 604/43 |
| 545358 | 2/1973 | U.S.S.R. | 604/43 |

*Primary Examiner*—Randall L. Green
*Assistant Examiner*—K. M. Reichle
*Attorney, Agent, or Firm*—Linval B. Castle

[57] ABSTRACT

A catheter and fluid pumping apparatus and the method for bypassing portions of the heart to temporarily reduce the work load on the heart muscle. A double tube catheter is introduced into the femoral vein or artery and is advanced into the ventricle where blood is drawn and mechanically pumped back into the heart at a position downstream, such as the aorta or the pulmonary artery. The desired cardiac circulation can be maintained while relieving the load on the heart muscle to enable it to rebuild its strength.

8 Claims, 3 Drawing Sheets

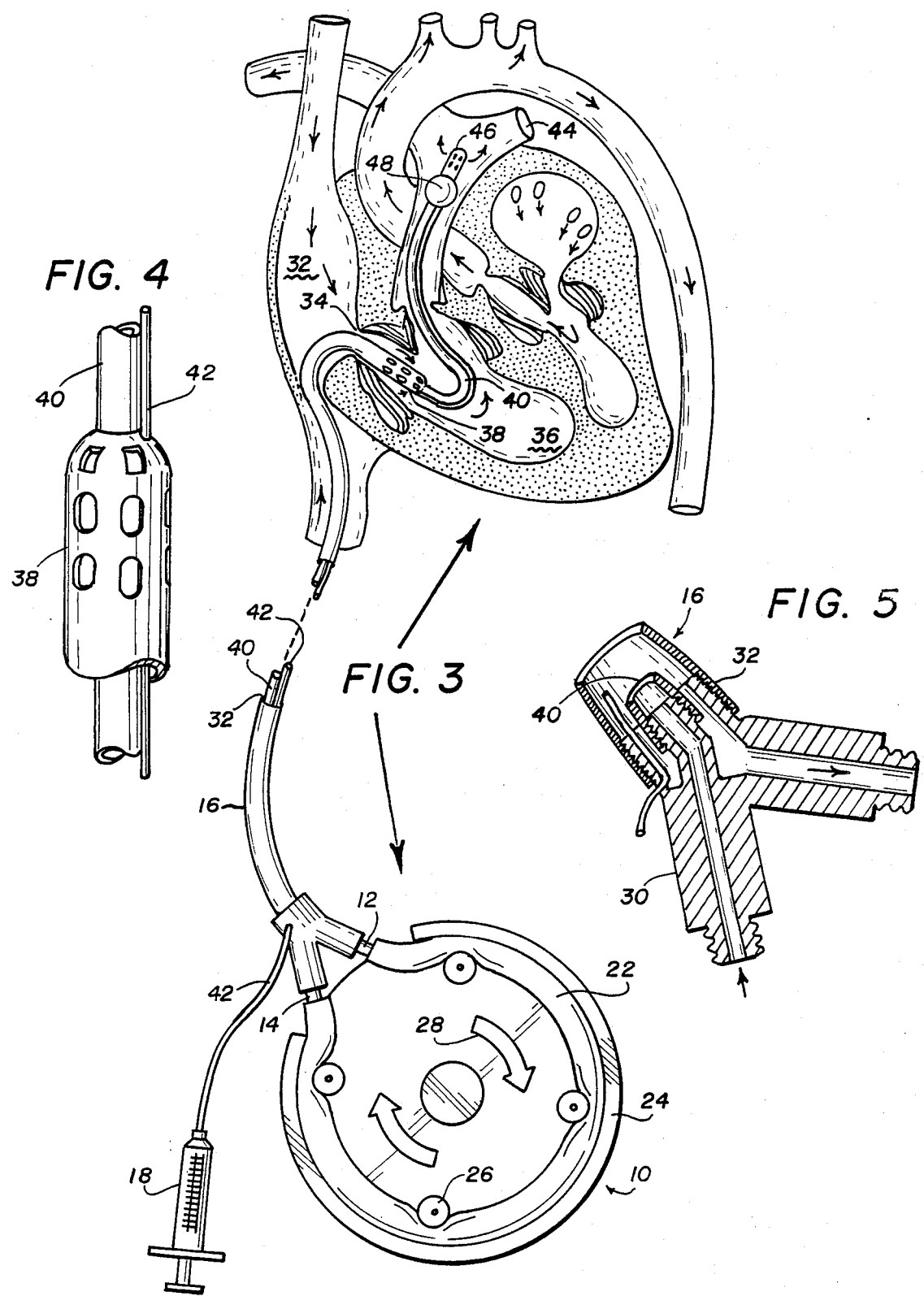

VENTRICULAR VENTING LOOP

BRIEF SUMMARY OF THE INVENTION

This invention relates to a non-surgical method and apparatus for relieving a substantial amount of work load on the heart muscle by withdrawing a continuous flow of blood from one input chamber and mechanically pumping it directly into an output chamber, such as the pumping from the right ventricle directly into the pulmonary artery.

Heart failure following acute myocardial infraction, valvular diseases, unsuccessful coronary balloon angioplasty, or even after open-heart procedure is primarily due to markedly decreased performance of the heart muscle. It is the purpose of the apparatus and procedure to be described herein to provide normal or even increased coronary circulation in a nonambulatory patient while reducing the work load on the heart pump by 20% or more. It is believed that, unless seriously damaged, the heart of an adequately anticoagulated hospitalized patient operating at such a reduced work load will completely rebuild its strength within several days thus obviating the need for surgical treatment, possible further deterioration and death.

Many ventricular assist devices have been developed, many of which were designed to relieve the ventricle of its work load and to enhance coronary circulation. Most of these ventricular assist devices, such as the intra-aortic balloon pump, the archimedes pump and others are limited to assist only the left ventricle. In may instances, however, right ventricular failure may instigate the whole catastrophic event of heart failure.

During open heart surgery, the principle of venting the heart, especially the left ventricle, is a basic procedure. This technique requires a negligible amount of time and involves the insertion of additional cannula through the left atrium or pulmonary vein into the ventricle, through the left ventricular apex, or through the aortic root for preventing overdistention of a paralyzed heart.

In a compromised heart, following an acute myocardial infarction or a complicated open-heart operation, assisting the heart pump by decreasing its work load and increasing coronary circulation is the object of immediate therapeutic measures, either by drugs or mechanical devices. The ventricular venting loop (VVL) to be described provides as accessory pathway of cardiac output venting a fraction of the stroke volume continuously from the ventricle to the systemic circulation. In the case of right ventricular failure, the right ventricle is vented and the stroke volume is perfused back to pulmonary circulation. This venting loop is activated by a suitable pump, such as an electrically powered portable roller pump located near the patient.

The catheter in the ventricular venting loop (VVL) is introduced percutaneously by Seldinger technique into the femoral artery or vein. In left ventricular venting, the tip of a double-lumen catheter is advanced into the left ventricle while in right ventricular venting, the catheter tip with an inflated arterial balloon (as in the Swan-Ganz catheter) is allowed to flow with the blood stream to pass the right ventricle into the pulmonary artery. The catheter has spaced inflow and outflow ports that are coupled to silastic tubing wrapped around heads of the roller pump, the RPM of which can be regulated to provide a desired cardiac output.

BRIEF DESCRIPTION OF THE DRAWINGS

In the drawings which illustrate the preferred embodiment of the invention:

FIG. 3 is an enlarged detailed view of the right ventricular assist device of FIG. 1;

FIG. 4 is a detailed drawing illustrating the outer lumen terminal in the right assist device;

FIG. 5 is a sectional view illustrating the crux which couples the roller pump to the coaxial tubing to the outer lumen terminal.

DETAILED DESCRIPTION

Figures 1, 2:
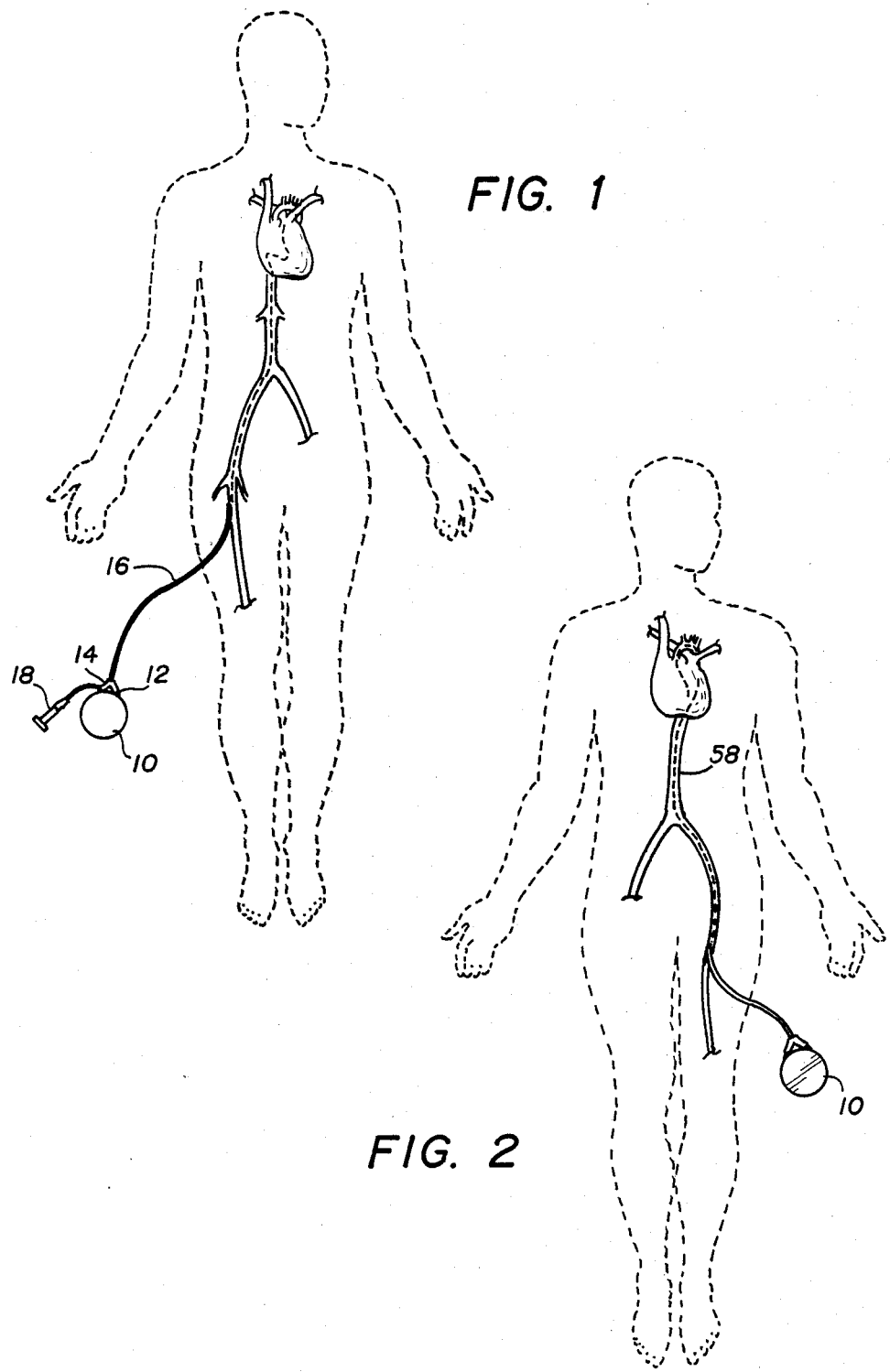
FIG. 1 is a phantom anatomic view of a human body illustrating the general positioning and location of a right ventricular assist device extending between a roller pump and through the femoral vein to the pulmonary artery.
FIG. 2 is a similar view of a left ventricular assist device extending from a pump and through the femoral artery to the left ventricle.

It will be appreciated that it is highly unlikely that any treatment of a patient will require the application of both a left and right ventricular assist devices as shown in FIGS. 1 and 2. However, both devices and procedures are described and claimed in this single patent document since the methods of use are identical and, except for a flow direction within the arterial tubing and an arterial balloon in the right venting loop, the instruments themselves are identical.

As illustrated in FIG. 1, the right ventricular assist device includes a portable motor driven pump 10 having an fluid inlet 12 and fluid outlet 14. The pump is coupled to a double lumen or coaxial tubing 16 about thirty inches in length, the outer tubing of the coaxial pair terminating in an inflow terminal several inches short of an outflow terminal in the end of the inner tubing as shown in FIG. 3. As used herein, the terms "double lumen" and "concentric tubing" refer to a small diameter tubing within a larger tubing; there is no requirement that the tubes actually be concentric or coaxial. Surrounding the outflow terminal is a small 2 cc. balloon which may be inflated and deflated as required through a very small tubing coupled to a 2 cc. syringe 18. In use, the outflow terminal of this catheter with its balloon deflated is introduced into the femoral vein 19. The balloon is then inflated with air and the coaxial tubing is drawn with the venous blood flow into the right ventricle of the heart and the inner tubing continues into the pulmonary artery. Operation of the pump 10 then acts to withdraw blood from the right ventricle and return the same blood into the pulmonary artery thus forming a right ventricular venting loop that bypasses the pulmonic valve and relieves the heart muscle of a portion of its normal work load.

The left ventricular assist device of FIG. 2 is nearly identical with that of FIG. 1, the difference being that the catheter in the left ventricular assist device will be forced against the blood flow and therefore does not use an arterial balloon. In FIG. 2, the motor driven pump 10 coupled to the concentric tubing receives its inflow through the inner tubing of the concentric pair and outflows through the outer tubing. The catheter is introduced into the femoral artery and is passed into the aorta and continues into the left ventricle. Rotation of the pump 20 operates to withdraw arterial blood from the left ventricle into an inflow terminal in the end of the inner tubing of the concentric pair and return the same blood into the aorta from the outflow terminal at the end of the outer tubing, thus forming a left ventricular venting loop that bypasses the aortic valve to relieve the heart muscle of a portion of its normal work load.

FIG. 3 is a detailed drawing illustrating the right ventricular assist device of FIG. 1 and shows the approximate positions of the inflow and outflow terminals within the heart to provide an effective venting loop.

The pump 10 of FIG. 3 is preferably driven by an AC/DC (battery) motor for portability and, in the preferred embodiment, is a roller pump employing a silastic tubing 22 confined between an outer ring 24 and a plurality of rollers 26 extending from the surface of a disc rotated by the AC/DC motor. As the motor rotates the disc in a direction shown by the arrows 28, the rollers squeeze the tubing 22 and its fluid contents from the inlet 12 to the outlet 14.

The pump 10 is coupled to a crux 30, shown in detail in the sectional drawing of FIG. 5. The crux is a hard plastic, Y-shaped coupling which couples the pump inlet 12 to the outer conduit of the coaxial tubing 16 and the pump outlet 14 to the inner conduit of the tubing 16.

As previously noted, the outer tubing 32 of the coaxial pair has an approximate inside diameter of 5/16 inch and, in use, extends from the crux 30, through the femoral vein, up through inferior vena cava into the right atrium 32 and through the tricuspid valve 34 into the right ventricle 36 where it terminates in a soft perforated inflow terminal 38 shown in greater detail in FIG. 4. In the preferred embodiment the terminal 38 is formed of PVC, but may be formed of materials such as silicone or polyethylene.

The inflow terminal 38 of FIG.4 merely seals the end of the outer tubing 32 around the inner tubing 40 and a very small air conduit 42 so that venous blood drawn in by the inflow terminal 38 located in the right ventricle 36 will be passed by action of the pump 10 through the pump and will flow through the the inner tube 40 of the concentric pair and out through the outflow terminal 46 into the pulmonary artery 44.

The inner tubing 40 is a soft lumen having an inside diameter of about ⅛ inch and is coupled between the crux 30 and its outflow terminal which comprises a blunt end portion with perforations at and surrounding the tip. Approximately a half inch behind the tip of the outflow terminal is a small 2 cc. balloon 48 that is inflatable and deflatable through the small air conduit 42 that extends through the inflow terminal 38 and outer tubing 32 with the inner tubing 40 to the crux 30 and to a syringe 18.

In use, the terminal end of the concentric tubing is introduced by Seldinger technique into the femoral vein and the balloon 48 is inflated with air by the syringe 18. The catheter, carefully monitored, is drawn by the balloon in the venous blood flow toward the heart and passes the inferior vena cava, the right ventricle and into the pulmonary artery and is thus positioned so that the inflow terminal of the system in in the ventricle and outflow is in the artery. The pump 10, when activated, thus relieves the heart muscle of much of its work load and permits the heart muscle to relax while blood continues to flow at a normal or even greater rate, depending upon the rotational velocity of the roller pump 10.

Figure 6:
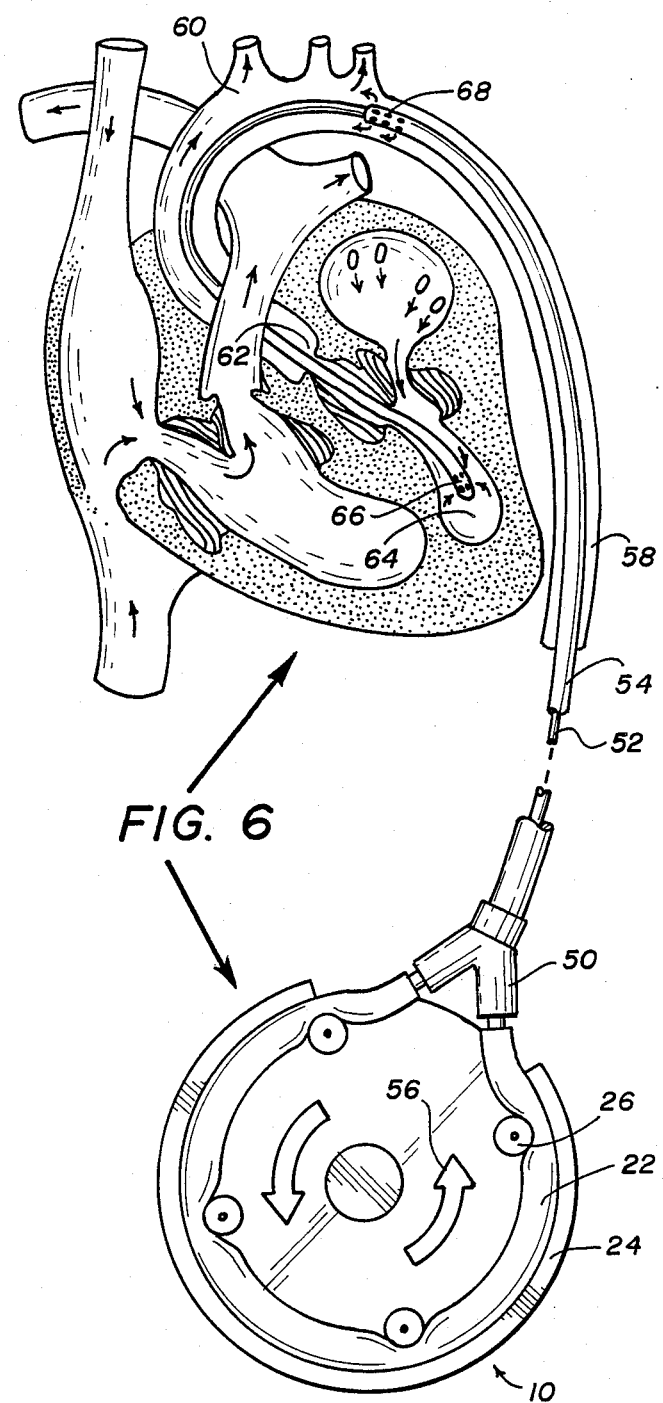
FIG. 6 is an enlarged detailed view of the left ventricular assist device of FIG. 2.

FIG. 6 is a detailed view illustrating the left ventricular assist device which, as in the right ventricular loop, employs the motor driven pump 10 coupled to a crux 50 which draws fluid into the pump through the inner tubing 52 of a lumen pair which includes the outer tubing 54. It will be noted that this flow is opposite to that described in connection with FIG. 3 and this is represented in FIG. 6 by reversing the direction of the pump 10 as shown by the arrows 56. If desired, the motor 10 of FIG. 6 may be rotated in a direction identical as that in FIG. 3, and that the correct inflow and outflow to the pump may then be controlled by the design of crux employed.

In this embodiment, the catheter is inserted into the femoral artery and, while fluoroscopically monitored, is moved through the descending aorta 58 into the aorta 60 and thence through the aortic valve 62 into the left ventricle 64. The inflow terminal 66 is at the distal end of the inner tubing 52 and is positioned in the left ventricle 64 to withdraw arterial blood which is pumped by the pump 10 through the outer tubing 54 to its outflow terminal 68 in the aorta 60. The ventricular venting loop thus formed bypasses an important and possibly overworked muscle of the heart to enable that ventricle to be relieved of its work load while continuing normal or even enhanced circulation.

I claim:

1. Ventricular assisting apparatus for bypassing portions of the heart while maintaining coronary circulation, said apparatus comprising:
   a variable output pump having a fluid input port and a fluid output port;
   a catheter having first and second conduits, each conduit having first and second ends, said catheter having diameter means substantially therealong for passage in femoral blood vessels and heart passages;
   the first end of said first conduit having fluid inflow terminal means for insertion through the blood stream of a patient and into the heart ventricle, the second end of said first conduit coupled to the fluid input port of said pump; and
   the first end of said second conduit having fluid outflow terminal means for insertion through said blood stream of said patient to a location downstream of said inflow terminal means, said second end of said second conduit coupled to the fluid output terminal means of said pump, whereby blood is withdrawn through the fluid inflow means form the heart ventricle, passed through the catheter and perfused through the fluid outflow means into the blood bypassing portions of the heart.

2. The apparatus claimed in claim 1 wherein said first and second fluid conduits are concentric.

3. The apparatus claimed in claim 2 wherein said pump is a roller pump.

4. The apparatus claimed in claim 2 further including a crux interposed between the second ends of said first and second conduits and said pump for directing fluid from said first conduit into the fluid input port and for directing fluid from the fluid output port into said second conduit.

5. The apparatus claimed in claim 1 wherein the first end of said second conduit includes a small balloon mounted therein and connected through a very small third balloon inflating air conduit to a syringe.

6. The apparatus claimed in claim 5 wherein said first conduit and said third balloon inflating conduit are located within said second conduit and wherein the inflation of said balloon in the femoral vein may draw the catheter with the blood flow through the right atrium and the heart right ventricle to a position in which the outflow terminal of said second conduit is in the heart pulmonary artery.

7. A method for temporarily relieving the work load of a heart muscle by withdrawing a fraction of blood flowing through a left heart ventricle and pumping it into the aorta, said method comprising the steps of:

providing a double luman catheter having first and second ends, percutaneously introducing the first end of the double lumen catheter into the femoral artery of a patient, said catheter further having a first conduit with respective first and second ends and an inflow terminal at its first end and a second conduit with respective first and second ends and an outflow terminal at its first end, said inflow terminal being axially spaced along said catheter from said outflow terminal;

advancing the inflow terminal of the first conduit of the double lumen catheter through the femoral artery, the descending aorta, the aorta and aortic valve into the left ventricle of the patient's heart while positioning the outflow terminal of the second conduit of the catheter in the aorta;

coupling the second end of said catheter to a controllable flow fluid pump having a fluid input port and a fluid output port with said first conduit coupled to the fluid input port for withdrawing blood from the left ventricle and said second conduit coupled to the fluid output port for pumping blood into said aorta; and actuating said fluid pump at a desired rotational speed to regulate cardiac output by withdrawing blood from the ventricle, passing it through the catheter and perfusing it into the aorta for circulation.

8. A method for temporarily relieving the work load on a heart muscle by withdrawing a fraction of blood flowing through a right heart ventricle and pumping it back into the pulmonary artery, said method comprising the steps of:

providing a catheter having first and second ends;

percutaneously introducing the first end of the catheter into the femoral vein of a patient, said catheter further having therein first and second conduits having respective first and second ends, and and a third air conduit said first conduit having an inflow terminal at its first end, said second conduit having an outflow terminal at its first end, said inflow terminal being axially spaced along said catheter from said outflow terminal;

and small inflatable balloon attached to the first end of said second conduit, and coupled to said third air conduit;

pneumatically inflating said balloon by injecting air through said third conduit;

advancing the first end of said second conduit and said balloon with the flow of blood through the femoral vein and right atrium into the pulmonary artery of the patient, and the first end of said first conduit into the right ventricle;

coupling the second end of said catheter to a controllable flow fluid pump having a fluid input port and a fluid output port with said first conduit coupled to the fluid input port and said second conduit coupled to the fluid output port of said pump; and actuating said pump at a desired rotational speed to withdraw blood from the right ventricle, pass it through said pump and perfuse it into the pulmonary artery for circulation.

* * * * *